United States Patent
Hu et al.

(10) Patent No.: US 10,738,051 B2
(45) Date of Patent: Aug. 11, 2020

(54) β-LACTAMASE INHIBITORS

(71) Applicant: QILU PHARMACEUTICAL CO., LTD., Jinan, Shandong (CN)

(72) Inventors: Boyu Hu, Shanghai (CN); Charles Z. Ding, Shanghai (CN); Zhigang Huang, Shanghai (CN); Ruibin Lin, Shanghai (CN); Minliang Xiao, Shanghai (CN); Jinsheng Xie, Shanghai (CN); Shuhui Chen, Shanghai (CN); Cheng Li, Shanghai (CN)

(73) Assignee: QILU PHARMACEUTICAL CO., LTD., Jinan, Shandong (CN)

( * ) Notice: Subject to any disclaimer, the term of this patent is extended or adjusted under 35 U.S.C. 154(b) by 11 days.

(21) Appl. No.: 16/305,414

(22) PCT Filed: Jun. 2, 2017

(86) PCT No.: PCT/CN2017/086999
§ 371 (c)(1),
(2) Date: Jan. 15, 2019

(87) PCT Pub. No.: WO2017/206947
PCT Pub. Date: Dec. 7, 2017

(65) Prior Publication Data
US 2020/0010467 A1  Jan. 9, 2020

(30) Foreign Application Priority Data
Jun. 3, 2016 (CN) .......................... 2016 1 0394846

(51) Int. Cl.
C07D 471/08 (2006.01)
A61P 31/04 (2006.01)

(52) U.S. Cl.
CPC ............ C07D 471/08 (2013.01); A61P 31/04 (2018.01)

(58) Field of Classification Search
CPC .................................................. C07D 471/08
See application file for complete search history.

(56) References Cited

U.S. PATENT DOCUMENTS

| | | |
|---|---|---|
| 2013/0225554 A1 | 8/2013 | Maiti et al. |
| 2014/0288051 A1 | 9/2014 | Maiti et al. |
| 2015/0141401 A1 | 5/2015 | Abe et al. |

FOREIGN PATENT DOCUMENTS

| | | |
|---|---|---|
| CN | 104334559 A | 2/2015 |
| CN | 104768951 A | 7/2015 |
| WO | 2012172368 A1 | 12/2012 |
| WO | 2014033560 A1 | 3/2014 |
| WO | 2014091268 A1 | 6/2014 |

OTHER PUBLICATIONS

International Search Report of PCT/CN2017/086999 dated Sep. 14, 2017.
Written Opinion of of PCT/CN2017/086999 dated Sep. 14, 2017.
Berge, S. et al., "Pharmaceutical Salts", Journal of Pharmaceutical Sciences, vol. 66(1), Jan. 1977, pp. 1-11.
Remington, The Science and Practice of Pharmacy, 21st Ed, Lippincott Williams & Wilkins (2005), USA.
Maehr, H., "A Proposed New Convention for Graphic Presentation of Molecular Geometry and Topography ", Journal of Chemical Education, vol. 62(2), Feb. 1985, pp. 114-120.
Blizzard, T. et al., "Discovery of MK-7655, a β-lactamase inhibitor for combination with Primaxin", Bioorg.Med.Lett., 2014(24), pp. 780-785.
Biondi, S. et al., "Currrent Trends in β-Lactam Based β-Lactamases Inhibitors", Current Medical Chemistry, 2011(18), pp. 4223-4236.
Qin, W. et al., β-Lactam Antibiotics Renaissance, Antibiotics, 2014(3), pp. 193-215.
Shlaes, D., "New β-lactam-β-lactamase inhibitor combinations in clinical development", Ann.N.Y.Acad.Sci. 2013(1277), pp. 105-114.
English translation of priority application No. CN 201610394846.7 (deemed to be withdrawn), 2016.

*Primary Examiner* — Bruck Kifle
(74) *Attorney, Agent, or Firm* — Harness, Dickey & Pierce, P.L.C.

(57) ABSTRACT

Disclosed in the present invention is a type of novel β-lactamase inhibitors, and specifically disclosed are a compound represented by formula (I) or a pharmaceutically acceptable salt thereof.

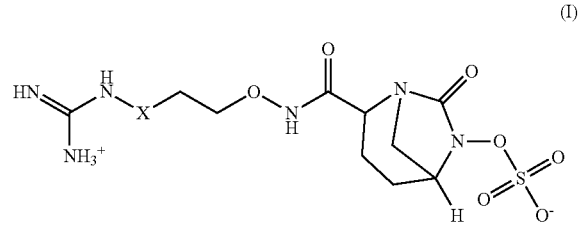

(I)

7 Claims, 1 Drawing Sheet

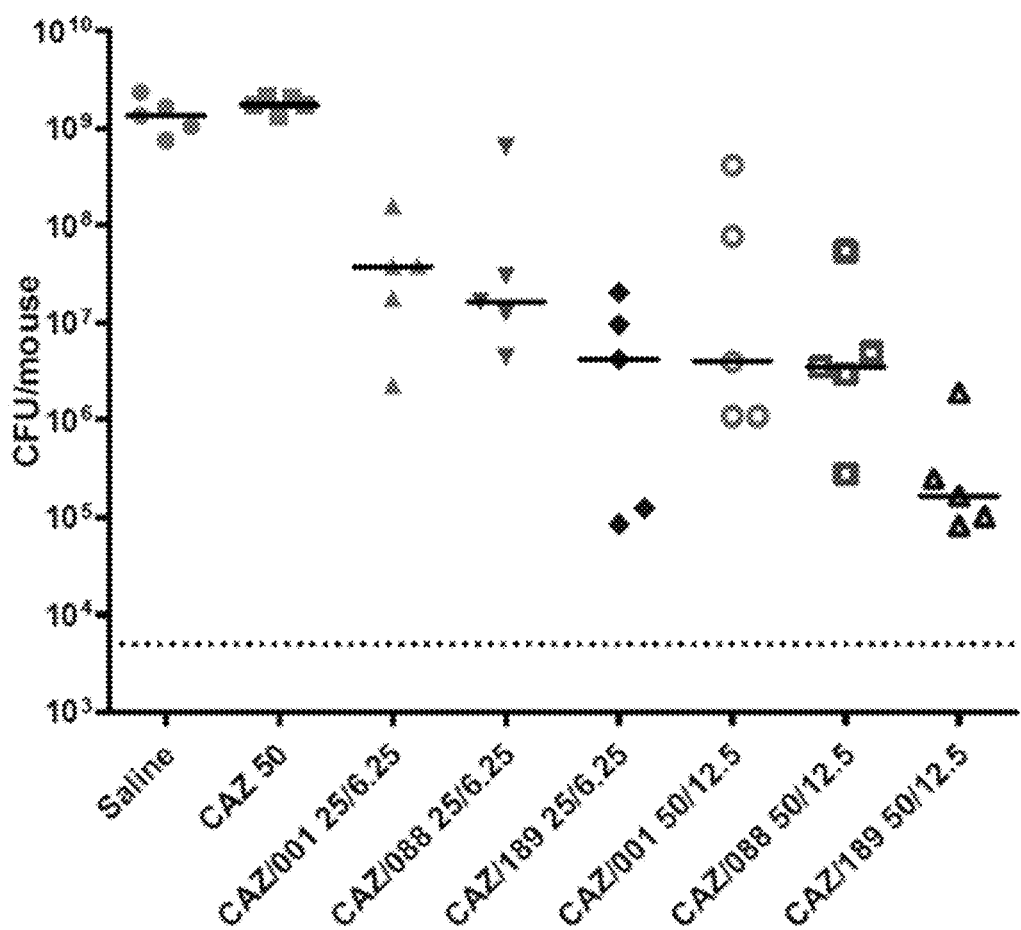

β-LACTAMASE INHIBITORS

CROSS REFERENCE TO RELATED APPLICATIONS

This application is a U.S. National Phase Application under 35 U.S.C. 371 of International Application No. PCT/CN2017/086999 filed on Jun. 2, 2017. This application claims priority to Chinese Application No. 201610394846.7, filed on Jun. 3, 2016. The entire disclosures of all of the above application are incorporated herein by reference.

FIELD OF INVENTION

The present invention relates to a novel class of β-lactamase inhibitors, specifically a compound represented by formula (I) or a pharmaceutically acceptable salt thereof.

PRIOR ARTS

β-lactam antibiotics have been used for more than 70 years and are widely used in clinic for the treatment of various infections. However, with the massive use and abuse of this class of drugs, bacterial resistance is also rapidly increasing. In the past 20 years, the situation faced by the physicians has become worse and worse, that is, the incidence and mortality of bacterial infections are rising rapidly in both communities and hospitals. There are two main pathogenic strains that are highly resistant to antibiotics and required for new therapeutic drugs. One is multidrug-resistant strains (MDR), which refers to bacteria that are resistant to three or more than three classes of commonly used antibacterial drugs. The other is extremely drug-resistant strains (XDR), which refers to bacteria that are resistant to almost all the commonly used antibacterial drugs. 30-50% of the nosocomial infections are caused by ESKAPE, which includes *Enterococcus faecium, Staphylococcus aureus, Klebsiella pneumoniae, Acinetobacter baumannii, Pseudomonas aeruginosa* and *Enterobacter* species. The above six classes of bacteria cover most MDR and XDR strains, which greatly limit the choice of physicians' treatment options.

There are several mechanisms by which bacteria develop resistance to β-lactam antibiotics, one of the principle mechanisms is the production of enzymes that can hydrolyze the β-lactam ring and inactivate the antibiotics. Bacteria can also selectively alter the target of antibiotics. For example, methicillin-resistant *Staphylococcus aureus* has developed multi-drug resistance which is associated with the production of new $PBP_{2a}$, increased synthesis of PBPs, and decreased drug affinity. β-lactamase can rapidly bind to certain enzyme-resistant β-lactam antibiotics, allowing the drug to remain in the extracellular matrix of the cytoplasm and fail to reach the target to exert an antibacterial effect. In addition, the outer membrane of G-bacteria is not easily permeable to certain β-lactam antibiotics, resulting in non-specific low-level resistance. There are also some active exocytosis systems on the cytoplasmic membrane of bacteria, by which bacteria actively exocytosis discharges drugs. Therefore, the combination of a β-lactam antibiotic and a β-lactamase inhibitor is the most clinically effective method. Bacteria can produce various types of β-lactamases, which can be classified into class A, B, C, and D according to their amino acid and nucleotide sequences. Class A, B, and D catalyze hydrolysis with serine as an active site, and class B enzymes cleave the ring by one or more than one metal atoms at the active site.

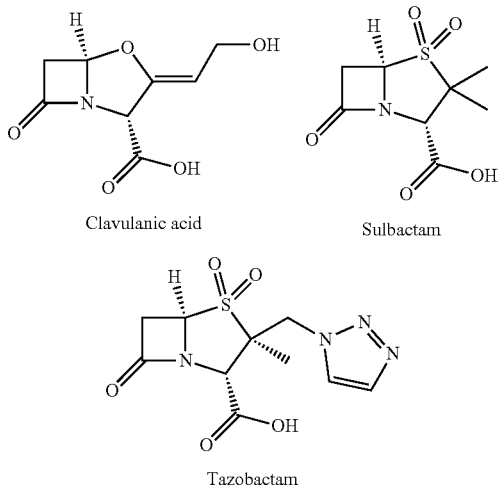

Clavulanic acid    Sulbactam

Tazobactam

The first well-known high-activity β-lactamase inhibitor is potassium clavulanate, and its combination with amoxicillin is still hot in the market to date. Two other important β-lactamase inhibitors on the market are sulbactam and tazobactam. These three drugs have a highly active β-lactam ring in their structure in common, which is the active site of these inhibitors. Although these three drugs are hot in the market, their antibacterial spectrum is very narrow. They only have an effect on class A and D β-lactamases, but are completely ineffective on class C enzymes and KPC enzymes which play an important role in class A enzymes.

In February 2015, FDA approved a new β-lactamase inhibitor called avibactam (NXL-104). This drug containing a novel diazabicyclo ring structure has a broader antibacterial spectrum than those three previous generation β-lactamase inhibitors described above. However, avibactam has a good inhibitory activity against class A β-lactamase but a relatively weak inhibitory activity against class C β-lactamase.

Diazabicyclic inhibitors will be a new direction in the development of β-lactamase inhibitors, especially for drugs that can achieve better inhibitory activity against both class A and class C β-lactamases which is still needed in the market.

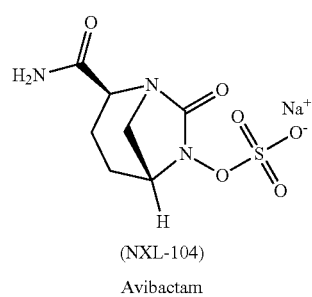

(NXL-104)
Avibactam

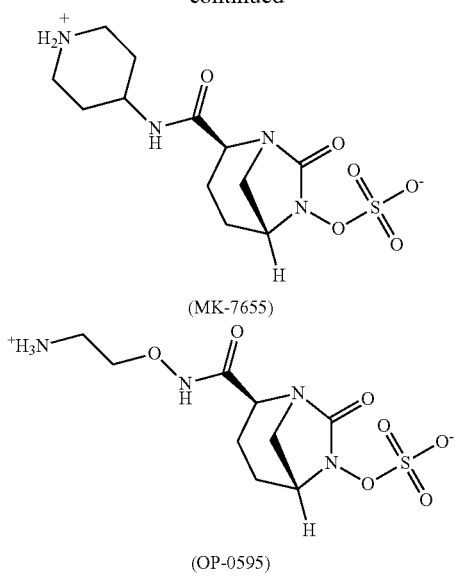

(MK-7655)

(OP-0595)

At present, antibiotic resistance has become a worldwide health problem, and new drug-resistant bacteria are emerging worldwide. With the slowdown in the development of antibiotics, the clinical antibacterial treatment is becoming more and more serious, and there is even a situation of "no medicine available". In view of this, it is imperative to develop new, safe and efficient β-lactamase inhibitors.

CONTENT OF THE PRESENT INVENTION

The present invention provides a compound represented by formula (I) or a pharmaceutically acceptable salt thereof,

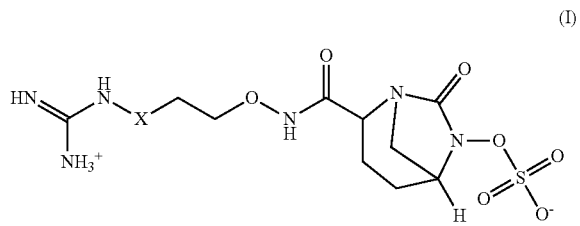

(I)

wherein,

X is O or N($R_1$);

$R_1$ is selected from the group consisting of $C_{1-6}$ alkyl, $C_{1-6}$ heteroalkyl, $C_{3-6}$ cycloalkyl, 3-6 membered heterocycloalkyl, and 5-6 membered aryl or heteroaryl, each of which is optionally substituted with 1, 2, or 3 R;

R is F, Cl, Br, I, CN, OH, $NH_2$ or COOH, or R is selected from the group consisting of $C_{1-6}$ alkyl, $C_{1-6}$ heteroalkyl, $C_{3-6}$ cycloalkyl, 3-6 membered heterocycloalkyl, phenyl and 5-6 membered heteroaryl, each of which is optionally substituted with 1, 2, or 3 R';

R' is F, Cl, Br, I, OH, CN, $NH_2$, COOH, Me, Et, $CF_3$, $CHF_2$, $CH_2F$, $NHCH_3$ or $N(CH_3)_2$;

"hetero" represents a heteroatom or a heteroatom group, which is selected from the group consisting of —C(=O)N(R)—, —N(R)—, —C(=NR)—, —S(=O)$_2$N(R)—, —S(=O)N(R)—, —O—, —S—, =O, =S, —O—N=, —C(=O)O—, —C(=O)—, —C(=S)—, —S(=O)—, —S(=O)$_2$—, and —N(R)C(=O)N(R)—;

in any of the above cases, the number of the heteroatom or the heteroatom group is independently 1, 2 or 3.

In some embodiments of the present invention, R is F, Cl, Br, I, CN, OH, $NH_2$, COOH, Me, Et, $CF_3$, $CHF_2$, $CH_2F$, $NHCH_3$, $N(CH_3)_2$ or methoxy.

In some embodiments of the present invention, X is O.

In some embodiments of the present invention, R is F, Cl, Br, I, CN, OH, $NH_2$, COOH, Me, Et, $CF_3$, $CHF_2$, $CH_2F$, $NHCH_3$, $N(CH_3)_2$ or methoxy, other variants are defined as above.

In some embodiments of the present invention, X is O, other variants are defined as above.

Other embodiments of the present invention are obtained by combining the above variables arbitrarily.

In some embodiments of the present invention, the compound or the pharmaceutically acceptable salt thereof is

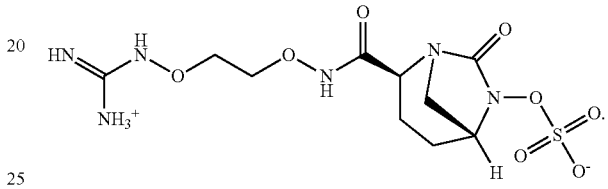

The invention also provides a pharmaceutical composition, which comprises a therapeutically effective amount of the compound or the pharmaceutically acceptable salt thereof as defined in the claim, and a pharmaceutically acceptable carrier.

The present invention also provides a use of the compound or the pharmaceutically acceptable salt thereof or the pharmaceutical composition in manufacturing a β-lactamase inhibitor for treating bacterial infection.

Advantageous Effect

The mother nucleus of the compound of the present invention introduces a novel side chain of guanidinoxy group on the diazabicyclo ring. Compared with the prior art, the group has more hydrogen bonding sites, thus has better physicochemical properties such as water solubility. On the other hand, the introduction of the guanidinoxy group makes pKa to 8.83, which is relatively close to the pKa of an amino group (e.g. the pKa of the amino group located at the lysine's terminal side chain is 8.95) and much smaller than the pKa of a guanidino group (e.g. the pKa of arginine is 12.48), thereby the compound can maintain good chemical stability. The experimental data in vitro and in vivo also showed that the introduction of the guanidinoxy group enables the compound of the present invention to inhibit various β-lactamases, and the bacteriostatic activity is remarkably enhanced. In the current situation where new clinical drugs are urgently needed to combat the increasingly severe infection of drug-resistant bacteria, the compound of the present invention is a highly promising drug that can solve the problem, which can exhibit better clinical effects in clinic.

Definition and Description

Unless otherwise indicated, the following terms and phrases used in this document are intended to have the following meanings. A specific term or phrase should not be considered indefinite or unclear in the absence of a particular definition, but should be understood in the ordinary sense.

When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "Pharmaceutical Salts", Journal of Pharmaceutical Science 66: 1-19 (1977)). Certain specific compounds of the present invention that contain both basic and acidic functional groups can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in an unsolvated form or a solvated form, including hydrated form. Generally, the solvated form is equivalent to the unsolvated form, and both are encompassed within the scope of the present invention.

Certain compounds of the present invention can have an asymmetric carbon atom (optical center) or a double bond. The racemate, diastereomer, geometric isomer and individual isomer are all encompassed within the scope of the present invention.

Unless otherwise specified, the absolute configuration of a stereogenic center is represented by a wedged solid bond ( and a wedged dashed bond () a wavy line () represents a wedged solid bond () or a wedged dashed bond (), and the relative configuration of a stereogenic center is represented by a straight solid bond () and a straight dashed bond (). When the compound described herein contains an olefinic double bond or other geometric asymmetric centers, E and Z geometric isomers are included unless otherwise specified. Likewise, all tautomeric forms are encompassed within the scope of the present invention.

The compound of the present invention may have a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound of the present invention may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field. The additional information about the carrier can be referred to *Remington: The Science and Practice of Pharmacy*, 21st Ed, Lippincott, Williams & Wilkins (2005), the disclosure of which is incorporated herein by reference.

The term "excipient" generally refers to a carrier, a diluent and/or a medium required for formulating an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxo (i.e. =O), it means two hydrogen atoms are substituted. Positions on an aromatic ring cannot be substituted with an oxo. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a substituent is attachable to more than one atom on a ring, such substituent can be bonded to any atom of the ring. For example, the structural unit

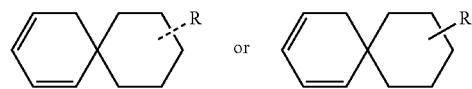

means that the substituent R can be located at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring. When the enumerative linking group does not indicate the direction for linking, the direction for linking is arbitrary, for example, the linking group L contained in

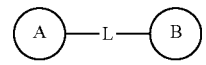

is -MW—, then -MW— can link ring A and ring B to form

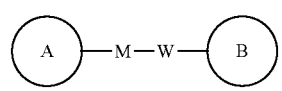

in the direction same as left-to-right reading order, and form

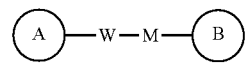

in the direction contrary to left-to-right reading order. A combination of the linking group, substituent and/or variants thereof is allowed only when such combination can result in a stable compound.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)p, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thieno-oxazolyl, thieno-thiazolyl, thieno-imidazolyl, thienyl, triazinyl, 1H-1,2,3-triazolyl, 2H-1,2,3-triazolyl, 1H-1,2,4-triazolyl, 4H-1,2,4-triazolyl, and xanthenyl. Also included are fused-ring compounds and spiro compounds.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon radical or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$, $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g. —$CH_2$F) or poly-substituted (e.g. —$CF_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, hexynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when combined with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxy, 3-(1-naphthyloxy) propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

All of the solvents used in the present invention are commercially available.

The present invention employs the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equal or equivalent; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol CBz represents benzyloxycarbonyl, which is an amino protecting group; BOC represents tert-butylcarbonyl, which is an amino protecting group; HOAc represents acetic acid; NaCNBH$_3$ represents sodium cyanoborohydride; rt represents room temperature; O/N represents overnight; THF represents tetrahydrofuran; Boc$_2$O represents di-tert-butyldicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(phenyl sulfonyl)benzenesulfonamide; NC S represents 1-chloropyrrolidin-2,5-dione; n-Bu$_4$NF represents tetrabutylammonium fluoride; iPrOH represents 2-propanol; mp represents melting point; LDA represents lithium diisopropylamide.

Compounds are named manually or by ChemDraw® software, the commercially available compounds use their vendor directory names.

BRIEF DESCRIPTION OF THE DRAWINGS

FIG. 1 shows the experimental result on *Klebsiella pneumoniae* strains which produce KPC β-lactamase.

DETAILED DESCRIPTION OF THE PREFERRED EMBODIMENT

The present invention will be specifically described below by way of embodiments, but the scope of the present invention is not limited thereto. The present invention has been described in detail herein, and the embodiment of the present invention has been disclosed herein. Various modifications and changes may be made to the embodiment of the present invention without departing from the spirit and scope of the invention, which will be apparent to the skilled in the art.

Embodiment 1: Compound 1

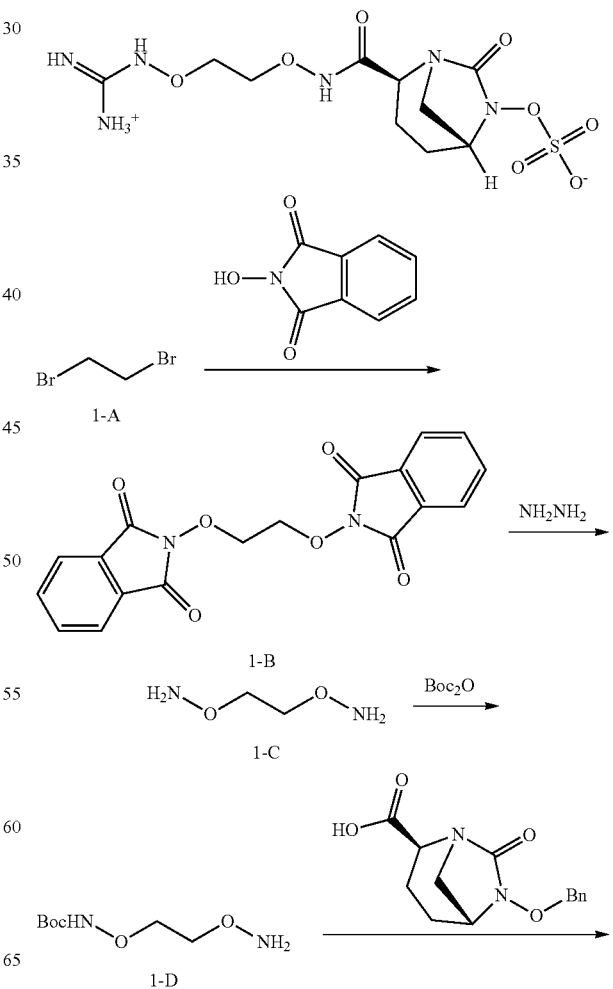

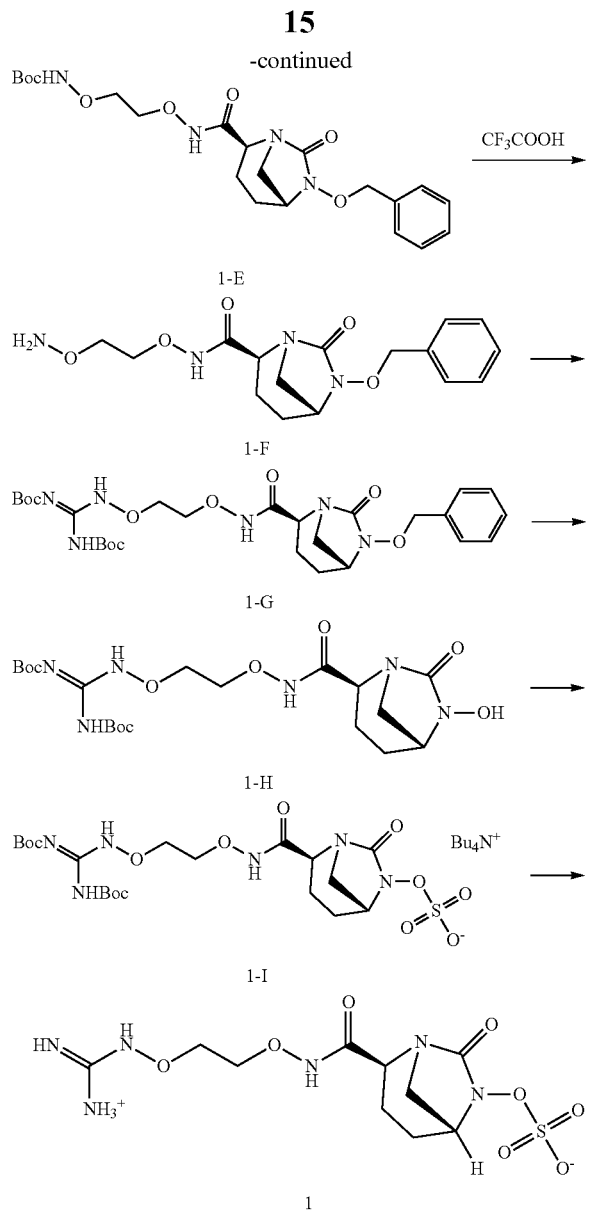

Step 3:

Compound 1-C (980 mg, 10.64 mmol) was dissolved in 50 mL dichloromethane and cooled to −10° C., then triethylamine (1.08 g, 10.64 mmol, 1.47 mL) was added by syringe, followed by dropwise addition of a solution of di-tert-butyl dicarbonate (2.32 g, 10.64 mmol) in 30 mL dichloromethane. The reaction solution was slowly warmed to room temperature (25° C.) and stirred for 20 hours. Then the reaction solution was evaporated and purified by silica gel column chromatography (ethyl acetate/petroleum ether, gradient is 30% to 50%) to give compound 1-D (700 mg, yield 34%).

Step 4:

Compound 1-D (300 mg, 1.56 mmol), (2S,5R)-6-(benzyloxy)-7-oxo-1,6-diazabicyclo[3.2.1]octane-2-carboxylic acid (431.23 mg, 1.56 mmol) (the synthesis method refers to WO2012172368A1), EDCI (388.77 mg, 2.03 mmol), HOBt (274.02 mg, 2.03 mmol) and diisopropylethylamine (201.62 mg, 1.56 mmol, 272.46 μL) were successively added to 20 mL dichloromethane. The reaction solution was stirred at room temperature (25° C.) for 20 hours, diluted with 30 mL dichloromethane, washed twice with 15 mL water, then washed with 15 mL brine. The organic phase was dried over anhydrous sodium sulfate, filtered and evaporated to dryness. The crude product was purified by silica gel column chromatography (ethyl acetate/petroleum ether, gradient is 30% to 50%) to give compound 1-E (262 mg, yield 67%).

Step 5:

Compound 1-E (760.00 mg, 1.69 mmol) was dissolved in dichloromethane (7.00 mL), followed by addition of trifluoroacetic acid (3.08 g, 27.01 mmol, 2.00 mL) at 20° C. The reaction solution was stirred for 3 hours, then evaporated, diluted with ethyl acetate (50 mL), washed with saturated sodium bicarbonate (50 mL) and saturated brine (50 mL). The organic phase was dried over anhydrous sodium sulfate, filtered and evaporated to give compound 1-F (410.00 mg, yield 65.68%).

Step 6:

Compound 1-F (200.00 mg, 570.83 μmol) and (E)-tert-butyl(tert-butoxycarbonyl)amino(methylene)carbamate (177.16 mg, 570.83 μmol) were dissolved in acetonitrile (2 mL). The reaction solution was stirred at 20° C. for 16 hours. After completion of the reaction, the reaction solution was evaporated and the residue was purified by silica gel column chromatography (ethyl acetate/petroleum ether=(0-2)/1 gradient elution) to give compound 1-G (300.00 mg, yield 86.91%).

Step 7:

Compound 1-G (300.00 mg, 506.21 μmol) was dissolved in isopropanol (3.00 mL)/water (3.00 mL), followed by addition of wet palladium carbon (50.00 mg, 10%). The mixture was stirred at 18-28° C. under hydrogen atmosphere for 2 hours, then filtered to give a solution of compound 1-H in isopropyl alcohol/water, which was used directly in the next step.

Step 8:

Sulphur trioxide trimethylamine complex (69.24 mg, 497.49 μmol) and triethylamine (10.07 mg, 99.50 μmol, 13.79 μL) were added to the solution of compound 1-H (250.00 mg, 497.49 μmol) in isopropanol (3.00 mL)/water (3.00 mL). The reaction solution was stirred at 18-28° C. for 16 hours. After completion of the reaction, the reaction solution was washed with ethyl acetate/petroleum ether (2/1, 6 mL, twice). The aqueous phase was collected and tetrabutylammonium bisulfate (168.43 mg, 496.07 μmol) was added, the mixture was stirred at room temperature for 0.5 hour, then extracted with ethyl acetate (15 mL, twice). The Step 1:

Starting material 1-A (50 g, 26.62 mmol), N-hydroxyphthalimide (8.69 g, 53.24 mmol) and triethylamine (6.73 g, 66.55 mmol) were dissolved in 100 mL N,N-dimethylformamide. The reaction solution was heated to 50° C. and stirred for 16 hours. Then the reaction solution was cooled to room temperature, poured into 100 mL ice water under stirring and filtered by suction. The filter cake was washed three times with 10 mL cold water and dried to give compound 1-B (9.3 g, yield 97%).

Step 2:

Compound 1-B (6.0 g, 17.03 mmol) was suspended in 400 mL dichloromethane and 150 mL methanol, and 85% hydrazine hydrate (1.71 g, 34.06 mmol, 1.66 mL) was added. The reaction solution was stirred at 25° C. for 18 hours, then filtered, and the filter cake was washed with 50 mL ethyl acetate. The filtrate was evaporated to dryness, and the residue was slurried with 40 mL petroleum ether/acetic acid (3:1), then filtered and further slurried twice. The filtrate was combined and evaporated to give compound 1-C (980 mg, yield 62%).

organic phase was washed with saturated brine (10 mL), dried over anhydrous sodium sulfate, filtered and evaporated to give compound 1-I (400.00 mg, 475.71 μmol, yield 95.89%).

Step 9:

Compound 1-I (200.00 mg, 242.71 μmol) was dissolved in anhydrous dichloromethane (2.00 mL), the solution was cooled to 0° C. under nitrogen atmosphere and trifluoroacetic acid (1.54 g, 13.51 mmol, 1.00 mL) was added, then the mixture was stirred for 2 hours. The reaction solution was stirred at 25° C. for another 4 hours and then evaporated under atmosphere. The residue was slurried three times with acetonitrile (2 mL) to give a crude product, which was purified by high performance liquid chromatography to give compound 1 (35.00 mg, yield 18.91%). $^1$HNMR (400 MHz, $D_2O$) δ 4.15 (s, 1H), 4.10-4.08 (m, 2H), 4.03-3.99 (m, 3H), 3.26 (d, J=12 Hz, 1H), 3.09 (d, J=12 Hz, 1H), 2.13-1.99 (m, 2H), 1.94-1.74 (m, 2H); LCMS (ESI) m/z: 383.1 (M+1).

Effect Embodiment 1: In Vitro Synergistic Inhibitory Concentration (SIC) Assay

The synergistic inhibitory concentration test was established based on the Clinical and Laboratory Standard Institute (CLSI) method M7, the initial concentration of the combined antibiotics was 128 μg/mL, which was serial diluted to a total of 11 serial dilutions, test concentration of active β-lactamase inhibitor was fixed at 4 μg/mL.

Experimental Objective:

This experiment was designed to evaluate whether the in vitro activity of the embodiment compound is superior to that of the reference compound OP-0595 or not, which was evaluated from two perspectives, one was that the embodiment compound restored the antibacterial activity of antibiotics or exhibited synergistic effect with antibiotics, the other was the antibacterial activity of the embodiment compound itself relative to antibiotics.

Experimental Method:

1) The test compound was dissolved (suspended if insoluble) in dimethyl sulfoxide and diluted to a concentration of 12.8 mg/mL as a stock solution, ceftazidime (CAZ) was dissolved in water and diluted to 25.6 mg/mL, ertapenem (ETP) was dissolved in phosphate buffered saline (PBS) and diluted to 25.6 mg/mL.

2) 30 μL dimethyl sulfoxide was added to columns 2-12 of the 96-V well plate. 60 μL prepared ceftazidime was added to column 1. 30 μL ceftazidime was transferred from column 1 to column 2 and mixed with a pipette. The same operation was continued until column 11, and 30 μL of the mixture in column 11 was discarded. This was the compound mother plate.

3) the test compound with a concentration of 12.8 mg/mL was diluted to 0.8 mg/mL with DMSO, then 30 μL was transferred to a column of the mother plate. Mix the liquid in the mother plate with a pipette.

4) One day before the experiment, the bacterial glycerol stock which was stored in a −80° C. refrigerator was streaked on a trypticase soy agar plate (TSA), and the plate was incubated in a 37° C. incubator overnight. On the day of the experiment, the monoclonal bacterial was suspended in physiological saline and the turbidity of which was adjusted to 0.5 McFarland standard, corresponding to $1\times10^8$ CFU/ml. This suspension was diluted 100-fold to $1\times10^6$ CFU/mL with caton-adjusted Mueller-Hnton broth (CAMHB), which was used as an inoculation fluid.

5) a 96-U plate was used as a test plate. Firstly, adding 98 μL CAMHB to each well of the test plate and transferring 2 μL solution in the mother plate to the test plate. 100 μL inoculation fluid was added to each well of the test plate. Each row of the test plate contained ceftazidime/test compound or ertapenem/test compound at a concentration of 128/4, 64/4, 32/4, 16/4, 8/4, 4/4, 2/4, 1/4, 0.5/4, 0.25/4, 0.125/4, 0/4 μg/mL.

6) The test plate was incubated at 37° C. for 20 hours. The minimum inhibitory concentration of ceftazidime was the lowest concentration that could completely or significantly inhibit the growth of bacterial.

The above-mentioned method was also used to determine the antibacterial activity of the test compound or the antibiotic when used alone. Table 1 showed the specific information of the β-lactamase-producing bacterial strain used in the experiment:

TABLE 1 the class and the source of β-lactamase-producing bacterial strain

| Class of bacterial strain | vendor code | β-lactamase-producing enzyme | class of enzyme |
| --- | --- | --- | --- |
| K. pneumoniae | ATCC 51503 | TEM-10/TEM-12 | A |
| K. pneumoniae | ATCC 51504 | TEM-10 | A |
| K. pneumoniae | ATCC BAA-205 | TEM-1/SHV-1/SHV-12 | A |
| K. pneumoniae | ATCC BAA-2343 | KPC-type | A |
| E. coli | ATCC BAA-2340 | KPC-type | A |
| K. pneumoniae | ATCC BAA-1705 | KPC-type | A |
| K. pneumoniae | ATCC BAA-1899 | KPC-type | A |
| K. pneumoniae | ATCC BAA-1898 | KPC-type | A |
| K. pneumoniae | ATCC 700603 | SHV-18 | A |
| E. coli | ATCC BAA-198 | TEM-26 | A |
| E. coli | ATCC BAA-200 | SHV-4 | A |
| E. coli | CCUG 59353 | CTX-15 | A |
| E. coli | CCUG 59354 | CTX-15 | A |
| K. pneumoniae | ATCC BAA-2473 | NDM-1 | B |
| K. pneumoniae | ATCC BAA-2472 | NDM-1 | B |
| K. pneumoniae | ATCC BAA-2470 | NDM-1 | B |
| K. pneumoniae | NCTC 13439 | VIM-1 | B |
| K. pneumoniae | NCTC 13443 | NDM-1 | B |
| P. aeruginosa | NCTC 13437 | VIM-10; VEB-1 | B |
| E. coli | NCTC 13476 | IMP-type | B |
| K. pneumoniae | NCTC 13440 | VIM-1 | B |
| E. cloacae | ATCC BAA-1143 | AmpC | C |
| K. pneumoniae | ATCC BAA-1144 | AmpC | C |
| E. coli | ATCC BAA-2523 | OXA-48 | D |
| K. pneumoniae | ATCC BAA-2524 | OXA-48 | D |
| E. coil | ATCC 25922 | pan-susceptible | sensitive bacteria |
| K. pneumoniae | ATCC 43816 | pan-susceptible | sensitive bacteria |

Note 1:

The class of β-lactamase produced by the bacterial strain in Table 1 was derived from the public network information of the supplier;

Note 2:

"ATCC" was the abbreviation of "American Type Culture Colletcion",

"CCUG" was the abbreviation of "Culture Collection University of Goteborg", and

"NCTC" was the abbreviation of "NCTC National Collection of Type Culture".

The experimental result was shown in Table 2-3.

TABLE 2

Synergistic inhibitory effect of compound 1 and ceftazidime against bacteria (μg/mL)

| Class of bacterial strain | Class of enzyme | Compound 1 | OP-0595 | Ceftazidime | Ceftazidime combined with compound 1 | Ceftazidime combined with OP-0595 |
|---|---|---|---|---|---|---|
| K. pneumoniae ATCC 51503 | TEM-10/12 | >128 | >128 | >128 | 1 | 1 |
| K. pneumoniae ATCC 51504 | TEM-10 | >128 | >128 | >128 | 2 | 2 |
| K. pneumoniae ATCC BAA-205 | TEM-1/SHV-1/SHV-12 | 128 | >128 | 32 | <=0.0625 | <=0.0625 |
| K. pneumoniae ATCC BAA-1705 | KPC | 128 | >128 | >128 | 0.125 | <=0.0625 |
| K. pneumoniae ATCC BAA-1899 | KPC | >128 | >128 | >128 | 0.5 | 0.5 |
| K. pneumoniae ATCC BAA-1898 | KPC | >128 | >128 | >128 | 0.125 | 0.25 |
| K. pneumoniae ATCC-700603 | SHV-18 | >128 | >128 | 64 | 0.25 | 0.25 |
| E. cloacae ATCC BAA-1143 | AmpC | 16 | 4 | >128 | 0.25 | <=0.0625 |
| K. pneumoniae ATCC BAA-1144 | AmpC | 128 | >128 | >128 | <=0.0625 | <=0.0625 |

TABLE 3

Synergistic inhibitory effect of compound 1 and ertapenem against bacteria (μg/mL)

| Class of bacterial strain | Class of enzyme | Compound 1 | OP-0595 | Ertapenem | Ertapenem combined with compound 1 | Ertapenem combined with OP-0595 |
|---|---|---|---|---|---|---|
| K. pneumoniae ATCC BAA-2472 | NDM-1 | >128 | >128 | >128 | >128 | >128 |
| K. pneumoniae ATCC BAA-2470 | NDM-1 | >128 | >128 | >128 | 16 | 8 |
| E. coli ATCC BAA-2523 | OXA-48 | 8 | 16 | 8 | <=0.125 | <=0.125 |
| K. pneumoniae ATCC BAA-2524 | OXA-48 | >128 | >128 | 4 | <=0.125 | 0.5 |

Conclusion: The compound 1 can significantly restore the antibacterial activity of ceftazidime, exhibit a good synergistic antibacterial effect with ceftazidime. Compound 1 significantly enhanced the activity of ertapenem when combined with ertapenem, exhibit a good synergistic antibacterial effect.

Effect Embodiment 2: In Vitro Enzymatic Assay

Experimental Objective:

This experiment was designed to evaluate the advantage of the embodiment compound compared to OP-0595 on the inhibitory activity against β-lactamase.

Experimental Method:

TABLE 4

100 μL reaction system in enzymatic assay

| Enzyme | Final concentration of enzyme | Final concentration of substrate (Nitrocefin) | Reaction buffer |
|---|---|---|---|
| TEM-1 | 0.11 nM | 0.1 mM | 1 × PBS, pH 7.4, 0.1 mg/mL BSA |
| AmpC-EC | 1.98 uM | 0.1 mM | 1 × PBS, pH 7.4, 0.1 mg/mL BSA |
| SHV-8 | 67.64 nM | 0.1 mM | 1 × PBS, pH 7.4, 0.1 mg/mL BSA |

TABLE 4-continued

100 μL reaction system in enzymatic assay

| Enzyme | Final concentration of enzyme | Final concentration of substrate (Nitrocefin) | Reaction buffer |
|---|---|---|---|
| CTX-M-44 | 0.68 nM | 0.1 mM | 1 × PBS, pH 7.4, 0.1 mg/mL BSA |
| AmpC-PA | 1.18 nM | 0.1 mM | 1 × PBS, pH 7.4, 0.1 mg/mL BSA |
| OXA-2 | 68.40 nM | 0.1 mM | 1 × PBS, pH 7.4, 0.1 mg/mL BSA |
| OXA-9 | 1.00 nM | 0.1 mM | 1 × PBS, pH 7.4, 0.1 mg/mL BSA |

1) The compound was dissolved in DMSO to prepare a stock mother solution (12.8 mg/mL, using the method in effect embodiment 1);

2) Prepare buffer solution A (1×PBS, pH 7.4, 0.1 mg/mL BSA) for enzymatic assay;

3) The compound mother liquor was 4-fold serial diluted for 11 times with DMSO in a 96-well tip-bottom plate, which was used as a working solution. A 96-well flat bottom plate was used as a test plate, the corresponding reaction buffer was previously added to each well, followed by addition of a corresponding volume of the working solution (100 μM-0.095 nM and 0 nM). Wherein, EDTA-$Na_2$ was used as a control for the NDM-1 test at a concentration of 20 mM;

4) adding the corresponding β-lactamase, and the test plate was incubated at 37° C. for 5 minutes;

5) Adding 5 μL Nitrocefin (the final reaction volume was 100 μL), the absorbance OD490 of the reaction solution in the plate was measured by a microplate reader and the result was recorded, the absorbance was measured every minute over 30 minutes;

6) The microplate reader could give a curve of OD490 over time. The slope of the curve (Abs2−Abs1)/(T2−T1) was calculated by taking two data points Abs1 and Abs2 within the linear range of the curve.

7) The relative inhibition rate was calculated as follows: Slope (EC) was calculated under the condition of absence of an inhibitor, and Slop(S) was calculated under the condition of an inhibitor at a certain concentration.

$$\% \text{ relative inhibition} = \frac{\text{Slope}(EC) - \text{Slope}(S)}{\text{Slope}(EC)}$$

The relative inhibition rate and the corresponding concentration of the inhibitor were used to calculate the $IC_{50}$ value of the inhibitor on β-lactamase. In this experiment, the $IC_{50}$ was calculated using the formula of GraphPad Prism 5.0, log(inhibitor) vs. normalized response-Variable slope.

Remarks: PBS refers to phosphate buffer solution; BSA refers to bovine serum albumin.

The experimental result was shown in table 5.

TABLE 5 the inhibitory activity of the compound on β-lactamase

| $IC_{50}$, nM | OP-0595 | Avibactam | Compound 1 |
|---|---|---|---|
| TEM-1 (Class A) | 157.20 | 12.39 | 38.94 |
| KPC (Class A) | 239.10 | 13.6 | 43.13 |
| AmpC-EC (Class C) | 22.73 | 107.00 | 20.17 |
| CTX-M-44 (Class C) | 194.80 | 66.98 | 31.92 |
| AmpC-PA (Class C) | 343.00 | 213.70 | 98.63 |
| OXA-2 (Class D) | 3451 | 1489 | 1547 |
| OXA-9 (Class D) | 51711 | 3129 | 4995 |

Conclusion: compound 1 has a good inhibitory activity on both class A and class C β-lactamases.

Effect Embodiment 3: In Vitro Synergistic Inhibitory Concentration (SIC) Assay Against Chinese Clinical Isolates Experimental Objective:

This experiment was designed to evaluate the inhibitory activity of BLI ((3-lactamase inhibitor) compound 1 against main carbapenemases.

Experimental Method:

The broth microdilution method was used to determine the minimum inhibitory concentration (MIC) of antibacterial agents (with and without BLI lead compound) against clinical isolates of carbapenemase-producing strains.

1. Drug susceptibility test: according to the method of antimicrobial susceptibility test described in the 2016 edition of the US Clinical and Laboratory Standards Institute (CLSI) document, the MIC of commonly used antibacterial drugs against clinically isolated bacteria was determined by a broth microdilution method.

2. Strains: 8 KPC-2 carbapenemase-producing strains, 8 NDM-1 metalloenzyme-producing strains, and 6 OXA-181 carbapenemase-producing strains. All strains were clinically isolated *Klebsiella pneumoniae*.

3. Concentration: a total of 12 antimicrobial concentration ranging from 0.06 μg/mL to 128 μg/mL were set, the concentration of enzyme inhibitor was fixed at 4 μg/mL.

4. Quality control strains: quality control strains of the drug susceptibility test include *Escherichia coli* ATCC 25922 and ATCC 35218.

The experimental result was shown in Table 6.

TABLE 6 test result of compound 1 against Chinese isolates

| Strains (number) | antibacterial agent | criteria Sensitive | Drug resistance | MIC range μg/mL | $MIC_{50}$ μg/mL | $MIC_{90}$ μg/mL | drug resistance rate | sensitive rate |
|---|---|---|---|---|---|---|---|---|
| KPC-2 carbapenemase- producing | meropenem | S <= 1 | R >= 4 | 16-128 | 64 | 128 | 100 | 0 |
| | ceftazidime | S <= 4 | R >= 16 | 64-128 | >128 | >128 | 100 | 0 |
| | aztreonam | S <= 4 | R >= 16 | >128 | >128 | >128 | 100 | 0 |

TABLE 6-continued test result of compound 1 against Chinese isolates

| Strains (number) | antibacterial agent | criteria Sensitive | criteria Drug resistance | MIC range µg/mL | MIC$_{50}$ µg/mL | MIC$_{90}$ µg/mL | drug resistance rate | sensitive rate |
|---|---|---|---|---|---|---|---|---|
| strains (8 strains) | meropenem + compound 1 | S <= 1 | R >= 4 | <=0.06-0.125 | <=0.06 | 0.125 | 0 | 100 |
| | meropenem + avibactam | S <= 1 | R >= 4 | <=0.06-0.25 | 0.125 | 0.25 | 0 | 100 |
| | ceftazidime + compound 1 | S <= 4 | R >= 16 | <=0.06 | <=0.06 | 0.06 | 0 | 100 |
| | ceftazidime + avibactam | S <= 4 | R >= 16 | <=0.06-4 | 2 | 4 | 0 | 100 |
| | aztreonam + compound 1 | S <= 4 | R >= 16 | <=0.06-1 | <=0.06 | 1 | 0 | 100 |
| | aztreonam + avibactam | S <= 4 | R >= 16 | <=0.06-8 | 1 | 8 | 0 | 87.5 |
| NDM-1 metalloenzyme-producing strains (8 strains) | meropenem | S <= 1 | R >= 4 | 2-32 | 4 | 32 | 75 | 0 |
| | ceftazidime | S <= 4 | R >= 16 | >128 | >128 | >128 | 100 | 0 |
| | aztreonam | S <= 4 | R >= 16 | 0.5-128 | 64 | >128 | 100 | 0 |
| | meropenem + compound 1 | S <= 1 | R >= 4 | <-0.06-2 | <-0.06 | 2 | 0 | 87.5 |
| | meropenem + avibactam | S <= 1 | R >= 4 | 2-16 | 2 | 16 | 50 | 0 |
| | ceftazidime + compound 1 | S <= 4 | R >= 16 | <=0.06-16 | 0.125 | 16 | 12.5 | 87.5 |
| | ceftazidime + avibactam | S <= 4 | R >= 16 | >128 | >128 | >128 | 100 | 0 |
| | aztreonam + compound 1 | S <= 4 | R >= 16 | <=0.06 | <=0.06 | <=0.06 | 0 | 100 |
| | aztreonam + avibactam | S <= 4 | R >= 16 | <=0.06-1 | 0.125 | 1 | 0 | 100 |
| OXA-181 carbapenemase-producing strains (7 strains) | meropenem | S <= 1 | R >= 4 | 0.5-2 | 0.5 | 2 | 0 | 85.7 |
| | ceftazidime | S <= 4 | R >= 16 | 128 -> 128 | >128 | >128 | 100 | 0 |
| | aztreonam | S <= 4 | R >= 16 | >128 | >128 | >128 | 100 | 0 |
| | meropenem + compound 1 | S <= 1 | R >= 4 | <=0.06 | <=0.06 | <=0.06 | 0 | 100 |
| | meropenem + avibactam | S <= 1 | R >= 4 | <=0.06 | <=0.06 | <=0.06 | 0 | 100 |
| | ceftazidime + compound 1 | S <= 4 | R >= 16 | <=0.06 | <=0.06 | <=0.06 | 0 | 100 |
| | ceftazidime + avibactam | S <= 4 | R >= 16 | <=0.06-1 | 1 | 1 | 0 | 100 |
| | aztreonam + compound 1 | S <= 4 | R >= 16 | <=0.06 | <=0.06 | <=0.06 | 0 | 100 |
| | aztreonam + avibactam | S <= 4 | R >= 16 | 0.125-0.5 | 0.125 | 0.5 | 0 | 100 |

Conclusion: The combination of compound 1 and an antibiotic exhibited strong antibacterial activity against KPC-2, NDM-1 or OXA-181 type carbapenemase-producing Klebsiella pneumoniae which is clinically isolated. Especially for NDM-1 type carbapenemase-producing bacteria, the inhibitory activity of compound 1 was significantly better than that of avibactam.

Effect Embodiment 4: Mouse Lung Infection Model

Experimental Objective:

This experiment was designed to determine whether the embodiment compound has pharmacological effects in a mouse lung infection model and further evaluate whether the embodiment compound has a significant advantage over the reference compound OP-0595 on pharmacological effect.

Experimental Materials:

Female CD-1 mice of about 7 weeks old, weighing 26-28 g; cyclophosphamide was injected at a dose of 150 mg/kg 4 days before infection, and further 100 mg/kg 1 day before infection; the bacteria infected was Klebsiella pneumoniae (ATCC BAA-1705, KPC-2). Compound 1 and the reference compound OP-0595 were synthesized in the laboratory.

Experimental Procedure:

Female CD-1 mice were infected with Klebsiella pneumoniae by intranasal instillation. Each mouse was instilled with 50 µL bacterial fluid through nasal cavity at a dose of 3.14E+07 CFU per mouse. At 2 h, 4 h, 6 h and 8 h after infection, each group of mice were treated with a corresponding compound or combined compounds by intraperitoneal injection.

At 10 h after infection, the mice in group 1, 2 and 3 were euthanized, and the lung was taken out and placed in a 50 mL centrifuge tube containing 10 mL sterile normal saline, the tube was placed on wet ice and transferred to BSL-2 laboratory for CFU counting. At 20 h after infection, the mice in group 4, 5 and 6 were euthanized and treated according to the same procedure.

The lungs were ground with an IKA T10 homogenizer (the maximum speed was 20S, repeated once). The homogenate was diluted in a gradient and spotted on a tryptone soy agar plate. The plate was placed in a 37° C. incubator for bacterial incubation. After 24 hours, the plate was taken out and the number of single colonies grown in each homogenate with a gradient dilution, and the amount of bacterial load in the lung of each mouse was calculated.

Experimental Scheme:

TABLE 7 efficacy evaluation of compound 1 and reference compound OP-0595 in mouse thigh muscle infection model

| Group | Class of strains | dosage | administration route | Experimental procedure | Number of mice |
|---|---|---|---|---|---|
| 1 | *Klebsiella pneumoniae* (ATCC BAA-1705, KPC-2) | normal saline | intraperitoneal injection (ip) | After bacterial infection, the first dose was administrated after 2 hours, the second dose was administrated after the 10th hour, and the amount of bacterial load in the lung of each group of mice was checked at the 24th hour. | 4 |
| 2 | | ceftazidime (50 mpk) | | | 5 |
| 3 | | ceftazidime (25 mpk) & avibactam (001) (6.25 mpk) | | | 5 |
| 4 | | ceftazidime (25 mpk) & OP-0595 (088) (6.25 mpk) | | | 5 |
| 5 | | ceftazidime (25 mpk) & compound 1 (189) (6.25 mpk) | | | 5 |
| 6 | | ceftazidime (50 mpk) & avibactam (001) (12.5 mpk) | | | 5 |
| 7 | | ceftazidime (50 mpk) & OP-0595 (088) (12.5 mpk) | | | 5 |
| 8 | | ceftazidime (50 mpk) & compound 1 (12.5 mpk) | | | 5 |

The experimental result was shown in FIG. 1.

Conclusion: It can be seen from the result that the amount of bacterial load in group of compound 1 in the mouse model was reduced by 0.5-1.5 logs than that in the reference group of compound OP-0595 at two different dosage. Compound 1 was significantly more potent than the reference compound OP-0595.

What is claimed is:

1. A compound represented by formula (I) or a pharmaceutically acceptable salt thereof;

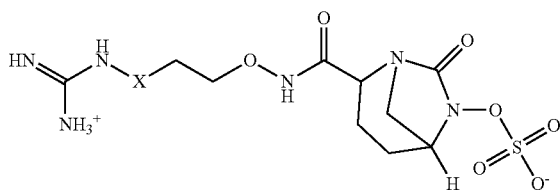

(I)

wherein,

X is O or $N(R_1)$;

$R_1$ is $C_{1-6}$ alkyl, $C_{1-6}$ heteroalkyl, $C_{3-6}$ cycloalkyl, 3-6 membered heterocycloalkyl, or 5-6 membered aryl and heteroaryl, each of which is optionally substituted with 1, 2, or 3 R;

R is F, Cl, Br, I, CN, OH, $NH_2$ or COOH, or R is selected from the group consisting of $C_{1-6}$ alkyl, $C_{1-6}$ heteroalkyl, $C_{3-6}$ cycloalkyl, 3-6 membered heterocycloalkyl, phenyl and 5-6 membered heteroaryl, each of which is optionally substituted with 1, 2, or 3 R';

R' is F, Cl, Br, I, OH, CN, $NH_2$, COOH, Me, Et, $CF_3$, $CHF_2$, $CH_2F$, $NHCH_3$ or $N(CH_3)_2$;

"hetero" represents a heteroatom or a heteroatom group, which is selected from the group consisting of —C(=O)N(R)—, —N(R)—, —C(=NR)—, —S(=O)$_2$N(R)—, —S(=O)N(R)—, —O—, —S—, =O, =S, —O—N=, —C(=O)O—, —C(=O)—, —C(=S)—, —S(=O)—, —S(=O)$_2$- and —N(R)C(=O)N(R)—;

in any of the above cases, the number of the heteroatom or the heteroatom group is independently 1, 2 or 3.

2. The compound or the pharmaceutically acceptable salt thereof as defined in claim 1, wherein R is F, Cl, Br, I, CN, OH, $NH_2$, COOH, Me, Et, $CF_3$, $CHF_2$, $CH_2F$, $NHCH_3$, $N(CH_3)_2$ or methoxy.

3. The compound or the pharmaceutically acceptable salt thereof as defined in claim 1, wherein X is O.

4. The compound or the pharmaceutically acceptable salt thereof as defined in claim 1, which is

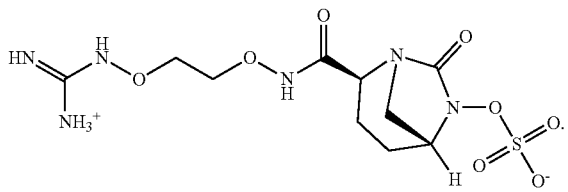 [SMILES: N=C([NH3+])NOCCONC(=O)[C@@H]1CC[C@@H]2CN1C(=O)N2OS(=O)(=O)[O-]]

5. A pharmaceutical composition, which comprises a therapeutically effective amount of the compound or the pharmaceutically acceptable salt thereof as defined in claim 1, and a pharmaceutically acceptable carrier.

6. A method for treating bacterial infection in a subject in need thereof, comprising administrating a therapeutically effective amount of the compound or the pharmaceutically acceptable salt thereof as defined in claim 1 to the subject.

7. A method for treating bacterial infection in a subject in need thereof, comprising administrating a therapeutically effective amount of the pharmaceutical composition as defined in claim 5 to the subject.

* * * * *